US012478803B2

(12) United States Patent
Dempsey et al.

(10) Patent No.: US 12,478,803 B2
(45) Date of Patent: Nov. 25, 2025

(54) SYSTEMS, METHODS AND COMPUTER SOFTWARE FOR OPTIMIZED RADIATION THERAPY

(71) Applicant: ViewRay Systems, Inc., Denver, CO (US)

(72) Inventors: James F. Dempsey, Pebble Beach, CA (US); Iwan Kawrykow, Sofia (BG)

(73) Assignee: ViewRay Systems, Inc., Denver, CO (US)

( * ) Notice: Subject to any disclaimer, the term of this patent is extended or adjusted under 35 U.S.C. 154(b) by 194 days.

(21) Appl. No.: 17/969,540

(22) Filed: Oct. 19, 2022

(65) Prior Publication Data

US 2023/0125812 A1 Apr. 27, 2023

Related U.S. Application Data

(60) Provisional application No. 63/270,855, filed on Oct. 22, 2021.

(51) Int. Cl.
*A61N 5/10* (2006.01)

(52) U.S. Cl.
CPC ......... *A61N 5/1039* (2013.01); *A61N 5/1049* (2013.01); *A61N 5/1071* (2013.01)

(58) Field of Classification Search
CPC .. A61N 5/1039; A61N 5/1049; A61N 5/1071; A61N 2005/1055; A61N 5/1048
See application file for complete search history.

(56) References Cited

U.S. PATENT DOCUMENTS 4,680,548 A 7/1987 Edelstein
4,774,468 A 9/1988 Bydder
(Continued)

FOREIGN PATENT DOCUMENTS

CN 1969194 A 5/2007
CN 101438959 A 5/2009
(Continued)

OTHER PUBLICATIONS

Yoganathan et al. 2019 Phys. Med. Biol. 64: 085016, 9 pages (Year: 2019).*
(Continued)

*Primary Examiner* — Keith M Raymond
*Assistant Examiner* — Patrick M Mehl
(74) *Attorney, Agent, or Firm* — Davis Graham & Stubbs LLP

(57) ABSTRACT

Systems, methods, and computer software are disclosed that allow the automatic recalling of imaging parameters from computer memory for controlling an MRI system to perform treatment-day scans of a patient on a treatment couch in a radiotherapy system, prior to treatment. The treatment-day scans can be automatically initialized and the MRI system can then be controlled to perform the treatment-day scans according to the recalled imaging parameters. Reoptimized radiation treatment plan(s) can be automatically generated and predicted doses to anatomical structures of the patient based on the plan(s) can be displayed. Clinicians can be enabled to perform numerous reoptimization tasks simultaneously through parallel workflow interfaces and then a radiation therapy device can be controlled to deliver radiation according to a selected radiation treatment plan.

22 Claims, 4 Drawing Sheets

(56) References Cited

U.S. PATENT DOCUMENTS 4,812,761 A 3/1989 Vaughan, Jr.
4,831,330 A 5/1989 Takahashi
5,184,076 A 2/1993 Ehnholm
5,477,146 A 12/1995 Jones
5,565,778 A 10/1996 Brey
5,594,342 A 1/1997 Brey
5,619,140 A 4/1997 Brey
5,621,323 A 4/1997 Larsen
5,990,681 A 11/1999 Richard
6,060,882 A 5/2000 Doty
6,100,694 A 8/2000 Wong
6,177,797 B1 1/2001 Srinivasan
6,198,957 B1 3/2001 Green
6,316,941 B1 11/2001 Fujita
6,366,798 B2 4/2002 Green
6,369,570 B1 4/2002 Wong
6,396,271 B1 5/2002 Burl
6,420,871 B1 7/2002 Wong
6,624,632 B2 9/2003 Iriguchi
6,930,480 B1 8/2005 Fujita
7,084,629 B2 8/2006 Monski, Jr.
7,221,161 B2 5/2007 Fujita
7,268,554 B2 9/2007 Vaughan
7,282,915 B2 10/2007 Giaquinto
7,397,246 B2 7/2008 Freytag
7,855,559 B2 12/2010 Defranco
7,907,987 B2 3/2011 Dempsey
7,911,209 B2 3/2011 Alradady
8,022,705 B2 9/2011 Bogdanov
8,035,384 B2 10/2011 Saha
8,129,992 B2 3/2012 Cork
8,217,653 B2 7/2012 Vaughan
8,331,531 B2 12/2012 Fahrig
8,427,158 B2 4/2013 Huish
8,497,682 B2 7/2013 Huish
8,704,520 B2 4/2014 Saha
8,710,843 B2 4/2014 Carlone
9,404,983 B2 8/2016 Dempsey
9,664,763 B2 5/2017 Amthor
10,043,284 B2 * 8/2018 Newell .................... G06T 7/70
10,107,878 B2 10/2018 Habara
10,466,319 B2 11/2019 Dempsey
2001/0001807 A1 5/2001 Green
2003/0071621 A1 4/2003 Watkins
2003/0122546 A1 7/2003 Leussler
2003/0146750 A1 8/2003 Vaughan
2003/0193380 A1 10/2003 De Swiet
2004/0140808 A1 7/2004 Vaughan
2005/0062472 A1 3/2005 Bottomley
2005/0099179 A1 5/2005 Monski, Jr.
2005/0231201 A1 10/2005 Fujimoto
2006/0033497 A1 2/2006 Chmielewski
2006/0033501 A1 2/2006 Vaughan, Jr.
2006/0273795 A1 12/2006 Rieke
2007/0007964 A1 1/2007 Vaughan, Jr.
2007/0016003 A1 1/2007 Piron
2007/0159170 A1 7/2007 Freytag
2007/0216409 A1 9/2007 Overweg
2007/0247158 A1 10/2007 Nistler
2007/0247160 A1 10/2007 Vaughan, Jr.
2008/0088309 A1 4/2008 Eberler
2008/0094063 A1 4/2008 Renz
2008/0100297 A1 5/2008 Ishii
2008/0129296 A1 6/2008 Fischer
2008/0275332 A1 11/2008 Alradady
2008/0278167 A1 11/2008 Vaughan, Jr.
2008/0306377 A1 12/2008 Piron
2009/0009169 A1 1/2009 Schulz
2009/0021256 A1 1/2009 Soutome
2009/0134873 A1 5/2009 Cho
2009/0134875 A1 5/2009 Tomiha
2009/0149735 A1 6/2009 Fallone
2009/0237077 A1 9/2009 Vaughan
2010/0033185 A1 2/2010 Saha
2010/0079139 A1 4/2010 Defranco
2010/0102811 A1 4/2010 Demas
2010/0164494 A1 7/2010 Koretsky
2010/0239066 A1 9/2010 Fahrig
2010/0253333 A1 10/2010 Zhai
2010/0253338 A1 10/2010 Eryaman
2010/0253350 A1 10/2010 Huish
2010/0253351 A1 10/2010 Huish
2011/0012593 A1 1/2011 Shvartsman
2011/0043207 A1 2/2011 Gross
2011/0125005 A1 5/2011 Misic
2011/0166437 A1 7/2011 Chang
2011/0215807 A1 9/2011 Misic
2011/0245978 A1 * 10/2011 Farrell .................. E05F 15/614
49/358
2012/0146643 A1 6/2012 Saha
2012/0150017 A1 6/2012 Yamaya
2012/0184841 A1 7/2012 Nielsen
2012/0268132 A1 10/2012 Zhu
2012/0286786 A1 11/2012 Schellekens
2012/0286921 A1 11/2012 Wang
2013/0027040 A1 1/2013 Alagappan
2013/0035584 A1 2/2013 Fahrig
2013/0131433 A1 5/2013 Katscher
2013/0165770 A1 6/2013 Li
2014/0043027 A1 2/2014 Overweg
2014/0084926 A1 3/2014 Amthor
2014/0125339 A1 5/2014 Lee
2014/0128719 A1 5/2014 Longfield
2014/0167758 A1 6/2014 Sambandamurthy
2014/0191757 A1 7/2014 Randell
2014/0221816 A1 8/2014 Franke
2014/0253126 A1 9/2014 Habara
2014/0266206 A1 9/2014 Dempsey
2014/0275962 A1 9/2014 Foo
2015/0054506 A1 2/2015 Eberler
2015/0112187 A1 4/2015 Petropoulos
2015/0177346 A1 6/2015 Mazurewitz
2015/0217136 A1 8/2015 Stanescu
2016/0146911 A1 5/2016 Chmielewski
2016/0216344 A1 7/2016 Habara
2016/0228728 A1 * 8/2016 Dempsey ............. A61N 5/1071
2016/0310761 A1 * 10/2016 Li ........................ A61N 5/1039
2017/0299671 A1 10/2017 Holle
2017/0307704 A1 10/2017 Leussler
2018/0085596 A1 * 3/2018 Peltola ................ A61N 5/1081
2018/0299520 A1 10/2018 Piron
2019/0310330 A1 10/2019 Yang
2019/0353724 A1 11/2019 Snelten
2020/0041587 A1 2/2020 Findeklkee
2020/0170596 A1 * 6/2020 Yu .......................... A61B 6/027
2021/0302514 A1 9/2021 Yang
2022/0120831 A1 4/2022 Yang

FOREIGN PATENT DOCUMENTS

CN 102711915 A 10/2012
CN 102713682 A 10/2012
EP 2345906 A1 7/2011
EP 2523011 A1 11/2012
EP 2589976 5/2013
GB 2424281 A 9/2006
JP 2002102207 4/2002
JP 2009142646 A 8/2009
JP 2012511382 5/2012
JP 2012236018 A 12/2012
WO 2005124379 A1 12/2005
WO 2008122899 A1 10/2008
WO 2009013650 A2 1/2009
WO 2011063342 A1 5/2011
WO 2011148278 12/2011

OTHER PUBLICATIONS

Sirag et al. 2015 Int. J. Eng. Res. & Sci. & Tech. 4:225-244 (Year: 2015).*

Strand et al. 2021 J. Appl. Clin. Med. Phys. 22:99â107 (Year: 2021).*

(56) References Cited

OTHER PUBLICATIONS

International Search Report issued in corresponding international application No. PCT/US2014/024354 mailed Jun. 12, 2014.

PCT/IB2022/057231 International Search Report and Written Opinion dated Nov. 14, 2022 (11 pages).

* cited by examiner

SYSTEMS, METHODS AND COMPUTER SOFTWARE FOR OPTIMIZED RADIATION THERAPY

RELATED APPLICATION(S)

This application claims priority to and the benefit of U.S. Provisional Application No. 63/270,855, filed Oct. 22, 2021, titled "Systems, Methods and Computer Software for Optimized Radiation Therapy," which is hereby incorporated by reference.

DESCRIPTION OF THE RELATED ART

Radiation therapy involves delivering radiation dose to a patient at a specific location to treat tissue, most typically cancerous tissue or tumors. To deliver radiation mainly to the target tissue and avoid irradiating healthy tissue, radiation beams are shaped and delivered in particular sequences and from particular directions according to a radiation treatment plan. In particular, optimization processes are used to mathematically determine the best radiation delivery parameters for the radiation treatment plan based on a radiation prescription determined by clinicians, patient imaging, radiotherapy device capabilities, etc. In some cases, the delivery of radiation can be guided by imaging prior to and/or during therapy and treatment plans can be improved through reoptimization.

SUMMARY

Systems, methods, and computer software relating to improved radiotherapy planning and treatment are disclosed. In one aspect, imaging parameters can be automatically recalled from computer memory for controlling an MRI system to perform treatment-day scans of a patient prior to treatment. The treatment-day scans can then be automatically initialized and the MRI system can be controlled to perform the treatment-day scans according to the recalled imaging parameters. A reoptimized radiation treatment plan can then be automatically generated and predicted doses to anatomical structures of the patient based on the reoptimized radiation treatment plan can be displayed. In some implementations, prescription doses to anatomical structures can be displayed concurrently with the displaying of predicted doses. Finally, a radiation therapy device can be controlled to deliver radiation according to a selected radiation treatment plan.

In some variations, the automatic initialization of the treatment-day scans can be based on a sensor indicating that a door to a treatment room is closed or the patient being sensed as being positioned at isocenter.

In some embodiments, the disclosed systems, methods, and software can provide for additional treatment plan reoptimization, including generation of a new reoptimized radiation treatment plan or modification of one of the automatically generated reoptimized radiation treatment plan(s). Furthermore, the disclosed systems, methods and software can enable clinicians to perform different reoptimization tasks simultaneously including through parallel workflow interfaces. This can include, for example, enabling multiple clinicians to perform autocontouring simultaneously or enabling clinicians to attempt different reoptimization strategies simultaneously. In yet other variations, an imaging plane can be moved based on user input and a reoptimized radiation treatment plan can be updated based on a new location of the imaging plane. Certain embodiments also allow for the receipt of user input modifying tracking parameters, dose parameters, structure shapes, or boundary parameters utilized by the system when controlling the radiation therapy device to deliver the radiation.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Figure 1:
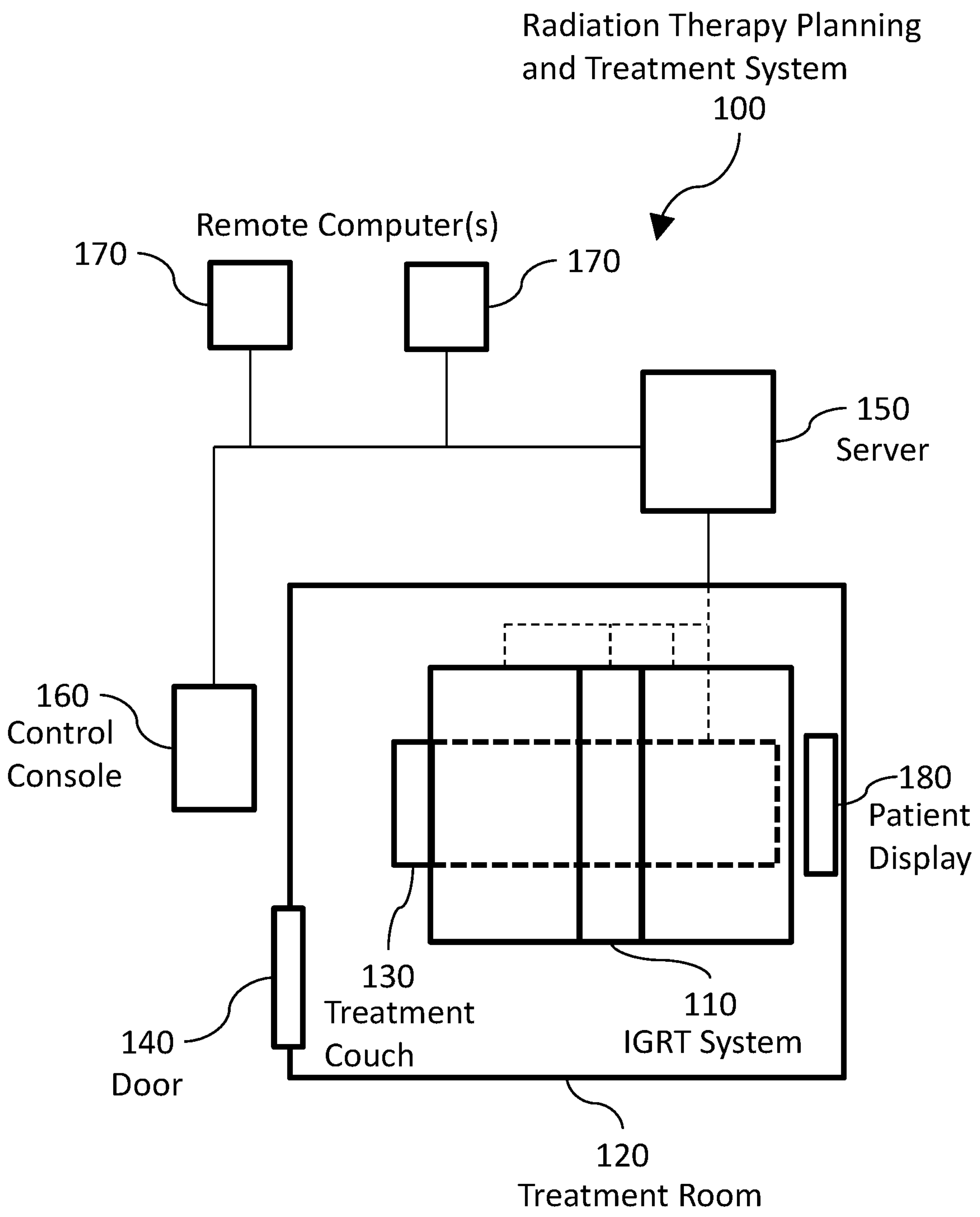
FIG. 1 is a simplified block diagram of an exemplary system for radiation therapy planning and treatment delivery in accordance with certain aspects of the present disclosure.

Conventional radiation therapy planning and delivery consists of several phases. Initially, the patient is imaged (e.g., with MRI and/or CT) to make a record of the patient's anatomy and identify target locations (e.g., tumors or regions of potential microscopic disease) for radiation treatment. The images are then reviewed by clinicians and a radiation treatment plan is determined. When it is time to treat the patient (which may be days or weeks later) the patient goes to a treatment facility and receives treatment according to the radiation treatment plan.

A simplified description of a radiation treatment plan is a sequence of operations performed by a radiation delivery device, typically in conjunction with an imaging system, to provide a prescribed dose to various locations of a patient's anatomy. A radiation treatment plan can include, for example, specifying angles of delivery for a radiation beam, beam-on times, beam collimator settings, patient couch positions, settings for imaging devices used during treatment delivery, etc. While the above is intended to provide a simplified introduction to radiation treatment plans, it is understood that an actual radiation treatment plans can have other aspects not specifically enumerated.

Adaptive radiation treatment provides for the changing or additional refinement of a radiation treatment plan based on current conditions of the patient. For example, if the patient gained or lost weight between the initial imaging and treatment day, the shape and location of the patient's healthy organs and targets can change from the original treatment plan. This can mean, for example, that the position of the treatment couch may need to be adjusted and the treatment plan may need to be reoptimized in order to deliver a clinically acceptable treatment plan.

Prior to the present disclosure, an adaptive radiation treatment required the physical presence of clinical team members such as physicians, physicists, dosimetrists, and therapists at the console of the radiation therapy system in a lengthy procedure to reoptimize a plan. For example, control of the therapy system was manually driven by a human operators performing the setting and acquiring of treatment day imaging, manually performing adaptive computations and performing evaluations of alternative treatment plans. Clinicians with different roles in the process, e.g., physicists and physicians, took turns reviewing and performing tasks required in an entirely sequential fashion, requiring coordination between them to perform the tasks. Many system settings and therapy decisions had to be made under time pressure with the patient waiting on the treatment couch.

As used herein, the terms "clinician," "physician," and the like, are provided to illustrate that many embodiments of the present disclosure are contemplated for use in a clinical setting to treat medical conditions of various patients. However, such terms should not be considered limiting and instead considered equivalent with the generic term "user," as the disclosed software can be utilized by any person.

As described in greater detail below, the present disclosure describes numerous image guided radiotherapy system and computer implemented processes that allow for improvements in adaptive radiotherapy processes thereby improving dose delivery, safety, efficiency and convenience in numerous processes.

Initial and pretreatment imaging scans can utilize any number and combination of different imaging types to characterize the patient for the delivery of radiotherapy. In some embodiments, the imaging types can include, for example, one or more of 2D planar, volumetric, 4D volumetric, and real-time 4D volumetric. 2D planar generally refers to a substantially planar slice through a patient (e.g., on axial, sagittal or coronal planes). Volumetric imaging generally refers to constructing a 3D patient volume depicting a region of the patient. 4D volumetric generally refers to volumetric (3D) images of the patient over time. For example, a 4D volumetric image can capture a patient volume at different times corresponding to a patient breathing cycle. In some implementations, 4D imaging can document breathing-cycle intervals, for example, as binned from some measure of the breathing cycle such as chest height or spirometer air volume. As such, the "times" for 4D volumetric imaging may not be a function of actual time. In contrast, "real-time" 4D volumetric imaging generally refers to 4D volumetric imaging that is reconstructed (and optionally provided to clinicians or made available to the radiation therapy system) in real time. As used herein, "real-time" means with minimal delay between image data capture and image development. In particular, the acquisition, reconstruction, and processing time can be less than the frame rate so that the imaging can keep pace with the procedure. In this way, the utilization of such real-time images can inform the clinician or the system about the nearly current state of the patient. In practice, implementations of real-time imaging can involve delays of less than one second and sometimes much less, e.g., 0.25 seconds to reconstruct and display a volumetric image. The required frame rate can depend on the speed of the motions being tracked in the patient, with 0.25 seconds being sufficient to resolve typical cardiac and respiratory motions.

The imaging needed to characterize patient anatomy for use on treatment day can be described with regard to what is referred to herein as "imaging parameters." Examples of imaging parameters can include contrast, dimensionality, frame rate, resolution, field of view, order of scanning, etc. Specific examples of the above can include, for example, contrast (e.g., T1/T2), dimensionality (e.g., 3D, 4D, real-time 4D), frame rate (e.g., 10 Hz, 4 Hz, 2 Hz), resolution (e.g., 0.5 mm, 1.0 mm, 2.0 mm), field of view (e.g., 30 cm DSV, 50 cm DSV, 75 cm DSV), order of scanning (e.g., any desired order of scanning axial, sagittal and coronal planes to generate images corresponding to any of the above-described imaging types), etc.

With the determination and acquisition of desired imaging parameters, the imaging parameters can be stored in a database or other computer system for recall at any time. For example, as described herein, the imaging parameters can be automatically recalled at a particular time on treatment day to have the needed imaging sequences prepared for execution with the patient before (or during) patient treatment.

FIG. 1 is a simplified block diagram of an exemplary radiation therapy planning and treatment system. As depicted, the radiation therapy planning and treatment system 100 can include an image guided radiation therapy (IGRT) system 110 located inside treatment room 120. Examples of IGRT systems can include medical linear accelerators (linacs), particle (protons, neutrons, etc.) therapy systems, or electron beam systems. Such systems can be guided by imaging systems such as MRI, CT, etc. The example imaging system shown depicts an open or split MRI where the radiation beam (e.g., delivered by a linac) is between the halves of the open MRI. The IGRT system may also include or incorporate a treatment couch 130 to support the patient within the IGRT system during treatment. The treatment couch can be configured to be adjustable in up to three dimensions (e.g., X, Y, Z) to position the patient at a desired location.

Treatment room 120 can be a vault or other enclosure that may be radiation shielded to prevent other portions of the facility from radiation generated by the radiation therapy device. The treatment room can also include magnetic and/or RF shielding to prevent external interference with the IGRT system and to prevent magnetic fields or RF from the IGRT system from escaping. Door 140 can be utilized to allow access to the treatment room. Such a door can have shielding similar to the treatment room to prevent the effects described above. As further described herein, door 140 can also include interlocks or other sensors to detect whether the treatment room door is closed.

One or more computing systems, diagrammatically simplified as server 150, can control the IGRT system and treatment couch. The server 150 can be located within the treatment facility or at a remote location. The server may be in wired and/or wireless communication with IGRT system 110, treatment couch 130, and/or more computers, e.g., control console 160 and one or more remote computers 170. In some embodiments, the server can be configured to operate as a web server and thus have the ability to cause the display of one or more radiation treatment plans or treatment delivery information at any combination of the control console and remote computers. Such displays of radiation treatment plans or other data from the server can be synchronized and in real-time thereby allowing users to interactively and collaboratively edit and/or approve radiation treatment plans. In certain embodiments, the server and software running thereon can require establishment of a secure connection before transmitting and/or receiving data relating to any of the operations described herein.

Control console 160 can be a workstation or other computing terminal that may be utilized by a clinician to control operation of the IGRT system. In some embodiments, the console can be proximate to the treatment room to allow the clinician providing treatment access to the IGRT system and the patient. In contrast, remote computer(s) 170 can be any connected computing system, for example, computers utilized by clinicians such as radiation oncologists or medical physicists that may not necessarily be proximate to the treatment room. Examples of remote computers can include, for example, desktop computers, notebook computers, tablet computers, smart phones, etc.

A patient display 180 can be included in some embodiments to allow the patient to observe the progress of treatment and allow them to assist in the positioning of their body during therapy. A patient display can be, for example, a computer screen or a visual projection onto a viewing surface or video-enabled goggles. Such screens or surfaces can be disposed within the MRI bore, or may be located outside the MRI system, but still viewable by the patient.

Figure 2:
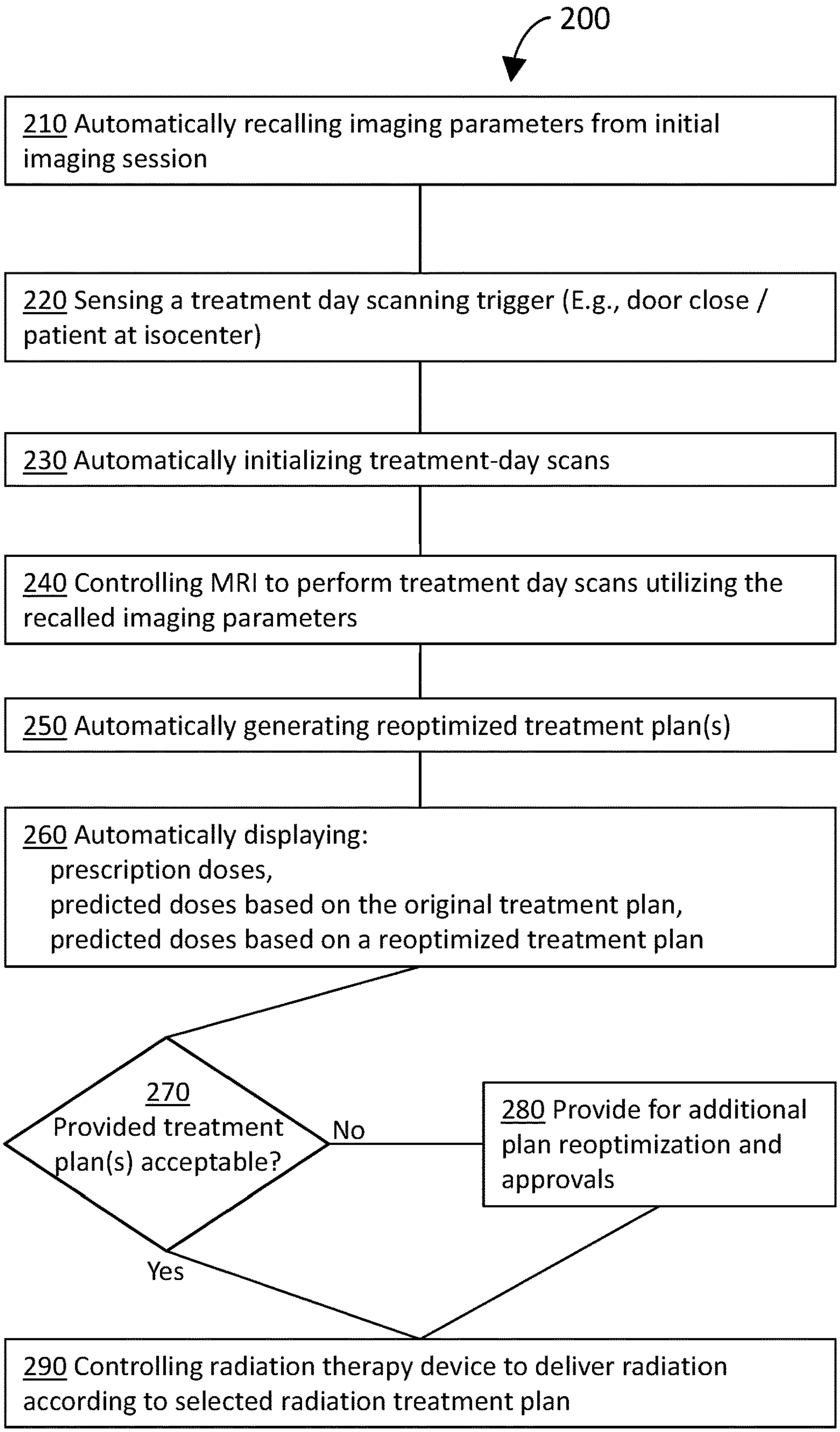
FIG. 2 is a flowchart of an exemplary software-implemented process for radiation therapy planning and treatment delivery in accordance with certain aspects of the present disclosure.

FIG. 2 is a flowchart of an exemplary process for radiotherapy implemented by software in conjunction with an image guided radiotherapy system. Process 200 is depicted as an example showing a number of features of the disclosed software, however, not every element of process 200 nor the depicted order is required.

Patient treatment can begin by the patient being brought to the treatment room and placed on the treatment couch. Clinicians may then secure the patient to prevent movement and thereby help ensure accurate delivery of radiation. The system may then proceed to automatically position the treatment couch at the appropriate location within the IGRT system. In some cases, this can include the treatment couch being translated into an imaging system such as an MRI. In other cases, such as for radiation sources utilizing a robotic arm, the treatment couch may remain substantially stationary.

Embodiments of the present disclosure can reduce the overall time to safely treat a patient by utilizing the disclosed software processes, such as the example process 200 in FIG. 2. This process can include, at 210, automatically recalling imaging parameters from computer memory (e.g., on server 150). These imaging parameters can be utilized (e.g., at 240, below) for controlling an MRI system to perform treatment-day scans of the patient on the treatment couch prior to treatment. The imaging parameters can include those determined from the process of obtaining the initial scans as described above. The imaging parameters can be loaded into the software that will perform treatment-day scans, such as server 150. The imaging parameters can optionally be displayed at control console 160 or any other connected computing system, such as remote computers 170.

Patient treatment can be sped up by the system automatically initializing the treatment-day scans based on sensing a treatment-day scanning trigger. For example, in certain embodiments, automatically initializing can be based on a sensor indicating that a door to the treatment room is closed. For example, there may be mechanical, electrical, or optical sensors that detect the closure and/or locking of the door to the treatment room. The output of such sensors can be converted to an electrical signal or status in a software system that can be utilized by the disclosed processes as a trigger to execute the initialization of the treatment-day scans.

In other embodiments, the automatic initializing can be based on sensing that the patient is at isocenter. For example, various IGRT systems can include sensors such as lasers, cameras, etc., that can detect the position of the patient relative to the isocenter. Such detection and analysis can be performed by image analysis, time-of-flight measurements, phase-shift translation registration algorithms, etc. For example, a phase shift translation registration algorithm can perform analysis of imaging of the patient taken during patient positioning and determine a best shift in the patient to align portions of the patient anatomy (e.g., a target tumor) to what it was in the initial imaging scans. In some embodiments, this can include limiting the field of view of these imaging scans to a fairly small region (e.g., 2-3 cm) in order to not skew a determined shift as a result of changes in other patient anatomy such as nearby organs. Once a needed shift is determined, in some cases, the patient may be asked to or assisted in physically moving to a location more proximate to isocenter. However, in other embodiments, the patient couch may be controlled by a computer to move the patient to isocenter based on the determined needed shift. In various embodiments, process steps 210 and 220 can be reversed. This means, for example, that the automatic recall of imaging parameters may not occur until the patient is ready for treatment as determined by a closed door to the treatment room or a determination of the patient is at isocenter.

The process may include, at 230, automatically initializing the treatment-day scans, for example after the sensing of a treatment-day scanning trigger as discussed above. The treatment-day scans can be initialized for execution according to the imaging parameters that were automatically recalled from the initial imaging session. The automatic recall of the imaging parameters can thus avoid extensive imaging parameters inputting by a clinician and also reduce the possibility of operator error.

The process may include, at 240, controlling the imaging (e.g., MRI) system to perform the treatment-day scans according to the recalled imaging parameters. For example, a sequence of scan planes, contrast types, etc., can be automatically and sequentially executed by the imaging system to provide imaging data analogous to the initial imaging session but capturing the patient's current anatomy.

Treatment-day scans may be performed to confirm the location of targets for radiation therapy as well as other anatomical structures that may have prescription limits on the amount of radiation they may receive (herein referred to as "organs at risk" (OARs). For example, in some cases the patient may undergo weight changes between treatment day and when they were initially scanned for generating the initial radiation treatment plan. Such changes in weight (or any other biological changes such as bladder or rectum fullness, inflammation, surgeries, etc.) can result in changes in shape and/or location of relevant anatomical structures of patient. With the treatment-day scans, the system can then proceed to perform or facilitate reoptimization or generation of radiation treatment plan(s) based on current patient conditions.

The process may include, at 250, automatically generating at least one reoptimized radiation treatment plan. In certain embodiments relating to treatment plan generation/reoptimization, "automatically" means that the generation of reoptimized radiation treatment plan(s) can occur prior to any assessment of the original treatment plan. For example, rather than a clinician determining that, based on treatment-day scans, reoptimization of the radiation treatment plan needs to be done, the system can automatically generate reoptimized radiation treatment plans based on the treatment-day scans. In some embodiments, the automatic generation can occur immediately (or with a small delay) when the treatment-day scanning is completed. However, it contemplated that in some systems there may be delays provided for various reasons. Accordingly, it is contemplated that while some embodiments of the present disclosure may have essentially zero or small delays (e.g., 1 second to perhaps 30 seconds), other embodiments may have delays up to several minutes, but nevertheless occur prior to assessment of the original treatment plan. Such longer days may not be optimal for rapid patient treatment but may be utilized in certain embodiments of the disclosed systems.

Further explanation and details of various embodiments of the system generating reoptimized radiation treatment plans are provided below with reference to FIG. 3. Also, any number of reoptimized radiation treatment plans can be generated by the system with the different plans having different constraints or utilizing different methods. In this way, multiple reoptimized radiation treatment plans can be provided and the best one (i.e., one most completely meeting the radiation prescription) can be selected either automatically by the system or by a user.

Processes consistent with the present disclosure may include (at step 260 in FIG. 2), displaying predicted doses to anatomical structures of the patient based on the reoptimized radiation treatment plan(s). In certain embodiments, the predicted doses may be automatically displayed without requiring any clinician input. The predicted doses can be provided for display at control console 110 and/or any of the remote computers 170. The displayed predicted doses can be in the form of, for example, heat maps, dose volume histograms, bar charts, etc. Predicted doses can include calculated quantities for what radiation doses will be delivered to various targets or other patient anatomy based on the corresponding imaging and the radiation delivery system. The predicted doses can be calculated, for example, utilizing methods such as Monte Carlo, pencil beam, convolution/superposition, discrete ordinates/Boltzmann transport, or any combination of the above.

The system can also store "prescription doses" that may include a list of targets and/or other patient anatomy (e.g., OARs) and an amount of radiation that the patient's physicians have determined should be delivered to each and optionally including an amount of tissue volume that will receive the radiation. The prescription doses can specify ranges, lower bounds, and/or upper bounds for such radiation doses. Such prescription doses can thus serve as a goal for radiation treatment plan reoptimization. This allows for acceptable variation in the acceptable treatment plan criteria considering the variations expected in the day-to-day changes in the patient.

Additionally, certain embodiments of the present disclosure can calculate and display prescription doses and/or predicted doses based on the original radiation treatment plan. In this way, both the newly generated reoptimized radiation treatment plan and (optionally) an original treatment plan can be compared to facilitate selection by clinicians, or by the system itself comparing plans, to determine which best meets the prescription.

The process may include, at 270, the system determining whether the provided treatment plan(s) (e.g., any of the original treatment plan and the generated reoptimized treatment plan(s)) are acceptable. For example, this can include the system performing comparisons with the predicted doses and the prescribed doses. If all prescriptions are met with the original treatment plan or the generated reoptimized treatment plan(s) then one (e.g., the best one) may be designated in the system as acceptable. If all prescriptions are not met, or it is determined that the provided radiation treatment plan(s) are not acceptable for any reason, then the process can provide for additional plan reoptimization as described below.

The process may include, at 280, providing for additional plan reoptimization and approvals. For example, in certain embodiments, the system can allow for a clinician to modify computer-generated contours of the patient anatomy (i.e., "auto" contours) to modify the predicted dose. In other embodiments, a relative electron density map can be modified, thereby changing the reoptimization. Details of these and further embodiments are described further below with reference to FIG. 3.

When a satisfactory reoptimized radiation treatment plan has been generated and approved by the requisite personnel or determined by the system to meet the prescription, treatment may commence as described at step 290, controlling a radiation therapy device to deliver radiation according to a selected radiation treatment plan. In some embodiments, the selected radiation treatment plan can be automatically delivered by the system, for example, as soon as a sufficiently good radiation treatment plan is available. In other embodiments, the selected radiation treatment plan can be delivered by the system in conjunction with commands originating from the control console (e.g., pressing a button to start treatment).

As previously mentioned, an imaging system, such as an MRI, can be configured to perform imaging during treatment by performing one or more of 2D imaging, multiplanar 2D imaging, 3D imaging, 4D imaging, and real-time 4D volumetric imaging, for example, based on previously recalled imaging parameters. In certain embodiments, controlling of the radiation therapy device can be further based on the imaging. Such dynamic controlling of the radiation delivery can account for patient motion and/or changes in patient anatomy. In certain embodiments, a collimating system, a rotating gantry supporting a radiation source, a configuration of a robotic arm supporting a radiation source, etc., can be adjusted to adaptively deliver radiation based on ongoing analysis of the imaging. In other embodiments, radiation delivery can be suspended for analysis and the subsequent resumption of delivery can be adjusted based on the imaging.

Additionally, certain embodiments of the present disclosure can automatically calculate and display the data and/or information for controlling the radiation therapy device based on the imaging. Examples of such data and/or information can include the imaging dimensionality, imaging parameters, tissue-tracking boundaries type and generation parameters, and the tissue-tracking algorithm parameters. The imaging dimensionality can indicate whether an image is 2D, 3D, real-time 40 volumetric, etc. An example of a tissue-tracking algorithm parameter can include denoising. Examples of tissue tracking boundaries type can include specifying whether it is a target, OAR, a boundary (e.g., an expanded region around the boundary where radiation may permissibly be delivered), boundary generation parameters can specify various tools to make a boundary, such as a free-drawing line, or a movable brush region that can expand/contract an existing boundary by pushing the boundary to not be inside the brush region.

Figure 3:
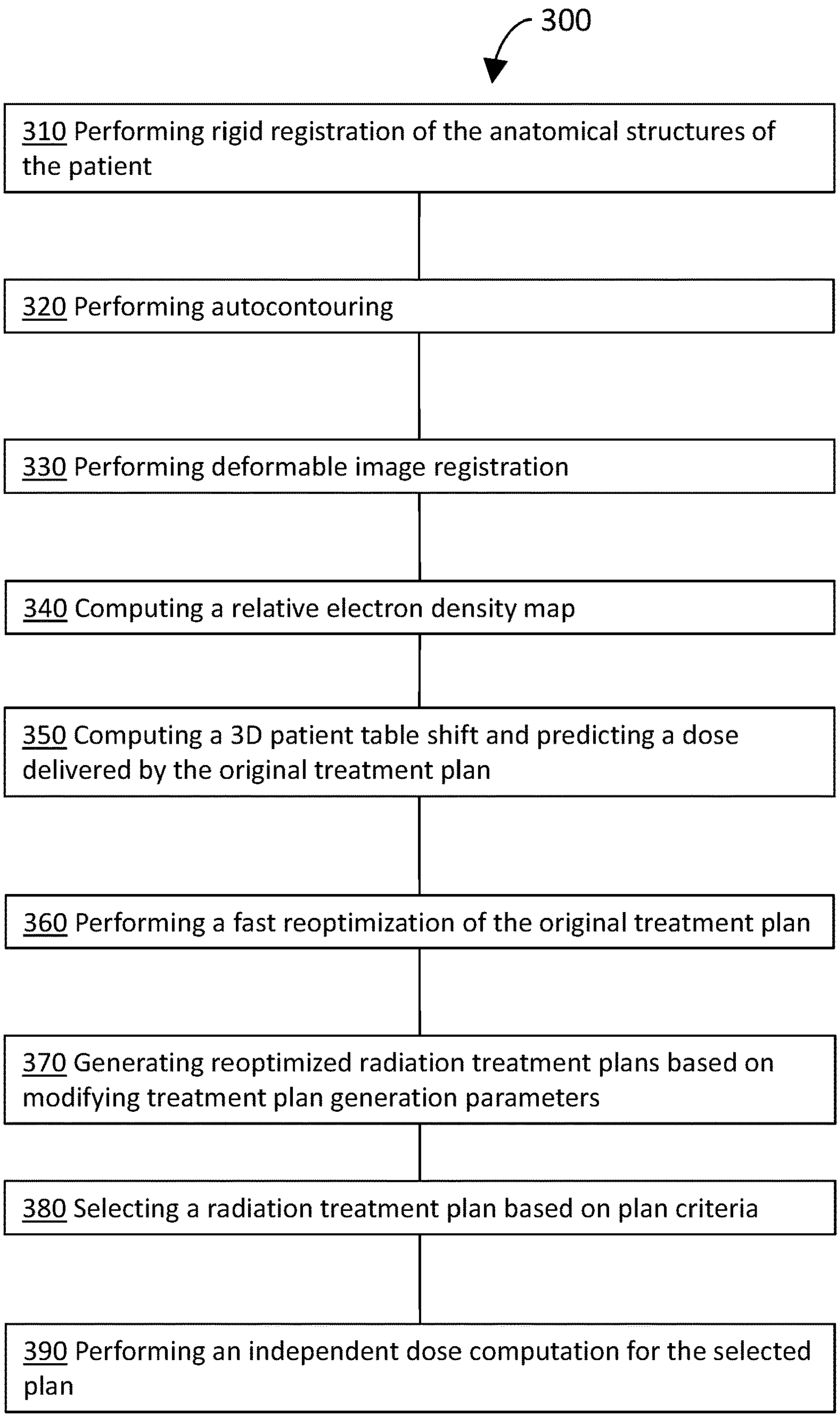
FIG. 3 is a flowchart of an exemplary software-implemented process for automatic radiation treatment plan reoptimization in accordance with certain aspects of the present disclosure.

FIG. 3 is a flowchart of an exemplary software-implemented process for automatic radiation treatment plan reoptimization (e.g., step 250 in FIG. 2). Process 300 describes one example of calculations that can be formed to generate and/or select a reoptimized radiation treatment plan. The elements in process 300 need not be executed in the order shown nor are all elements necessary in all embodiments.

Process 300 may include, at 310, performing a rigid registration of the anatomical structures of the patient. A rigid registration can include determining a shift (e.g., a patient couch shift) that improves the agreement between the current patient position and where the patient should be (e.g., locating a treatment target at isocenter). Determination of the shift can be calculated by the system utilizing image analysis techniques such as image differencing, image spectral cross-correlation, etc.

The process may include, at 320, performing autocontouring of the anatomical structures of the patient in the treatment-day imaging. Autocontouring can include the system determining edges around various anatomical structures in the patient images. These edges (or contours) thus define in 2D (or 3D) the predicted extents of the anatomical structures. Rather than a clinician having to view multiple frames of an image and manually drawing for determining contours, the system can be configured to determine (or autocontour) the anatomy by any number of methods. One exemplary method can include gradient analysis where gradients in the image are assumed to represent changes in the physical structure of the patient, e.g., a boundary between a tumor and healthy tissue.

The process may include, at 330, performing deformable image registration. Deformable image registration allows for nonrigid changes in patient anatomy when performing registration of the patient. For example, a shape of a tumor in a current image may be elongated relative to the shape in a prior image. The differences between pixels or voxels can be weighted to provide a best shift refinement such that despite the deformed image, the computed shift results in the best positioning of the patient for treatment. In other examples, deformable image registration can be used for a best alignment of sequential images that may have changed due deformations. For example, to construct a 4D patient volume for display or radiation treatment planning purposes, elements of a current volumetric image can be deformed to determine a shift to best align with a prior image.

The process may include, at 340, computing a relative electron density map. A relative electron density map (RED) can be used in generating a reoptimized radiation treatment plan to provide a more accurate dose computation as methods of ionizing radiation dose computation for megavoltage photon beams are most accurate when this information can be provided. A RED can be generated by, for example, setting segmented anatomy to known RED values (known as a RED structure override), applying deformable image registration to a RED derived from the patient or a template of a similar patient, by generating a synthetic CT from the MR image of the patient, or a combination of these methods.

The process may include, at 350, computing a 3D patient table shift and/or calculating predicted doses to the anatomical structures. As previously explained, various registration techniques can result in a determination for how the system needs to adjust the patient to locate them in the proper position for treatment. The calculated patient table shift can be any combination of X, Y, and Z shifts and rotations. In other embodiments, the calculations and/or shifting can be performed in 2D or 1D, though generally such shifts can be expressed as a 3D shift even if a shift in a particular direction is unneeded. Also, the predicted doses to anatomical structures can be calculated as described herein and utilized during any of the reoptimization processes disclosed herein.

The process may include, at 360, performing a fast reoptimization of the original radiation treatment plan, or an optimization of the beam intensities of a previously existing treatment plan. A "fast" reoptimization can utilize existing beam shapes and beam angles, which were previously computed to predict the dose that would be delivered by the prior radiation treatment plan. In other implementations, a "full" reoptimization can be performed that can include computing beamlets, performing fluence map optimization, and sequencing and reoptimization of an MLC leaf positions. Fast reoptimization thereby can have a reduced computational overhead and/or take less time to complete as compared to a full reoptimization.

The process may include, at 370, generating one or more reoptimized radiation treatment plans based on modifying treatment plan generation parameters. The system can be configured to receive input changing one or more features of the at least one reoptimized radiation treatment plan. In some cases, better realization of the radiation prescription can be achieved by changing one or more of the following features: the position of the patient couch, contoured anatomical structures, RED structure override values, or optimization objective functions and constraints. Examples of optimization objective functions and constraints can include penalty functions or operators such as >, ≥, <, <, or = for a dose volume objective and a weight for this objective, in addition to min, max, mean, and median objectives. The system can be configured to then automatically recalculate a reoptimized radiation treatment plan based on the changed features.

While the inputs that change a radiation treatment plan can be provided based on user input (e.g., using a graphical interface to change a contour, entering a new value for a target dose or tolerance), in some embodiments, such changes can be automatically implemented by the system software to generate a number of reoptimized radiation treatment plans. For example, one embodiment can have the automatic generating of reoptimized radiation treatment plan(s) include generating reoptimized radiation treatment plans based on modifying treatment plan generation parameters. The generating of the reoptimized radiation treatment plan(s) can stop when one of the reoptimized treatment plans meets a treatment prescription or when a predetermined number of reoptimized radiation treatment plans are generated.

As an example of how parameters can be varied to generate different radiation treatment plans, first the system can compare the predicted statistics (e.g., doses to anatomical structures) to the prescription. Then, for example, if a predicted dose is too low, a weighting, importance, or power (if using a power function penalty) can be increased in the objective function that is trying to deliver the prescribed dose to the target volume. As another example, if a critical organ is being overdosed, the weight, importance, or power of the objective attempting to spare the organs can be increased. Such optimizations can be performed in an iterative fashion to reach the target prescription or the closest possible convergence.

As mentioned above, any number of such reoptimized radiation treatment plans can be generated, for example, one, two, three, five, ten, etc. This predetermined number can be set or modified by a user as desired or can be hardcoded into the software. In some embodiments, the radiation treatment plans can be generated sequentially (i.e., one finishes and then is checked against the prescription before starting another). In other embodiments, the radiation treatment plans can be generated in parallel. In some embodiments, the system can stop plan generation when it is determined that one of the plans meets the prescription. For example, five radiation treatment plans can be started and if the third plan is completed and determined to meet the prescription then any uncompleted plans in progress may be ceased. Such implementations can have the benefit of reducing unnecessary computational overhead and further reducing the time required to commence treatment.

The process may include, at 380, selecting a reoptimized radiation treatment plan based on plan criteria (e.g., the prescription). In some embodiments, the software can be configured to allow a user to select from any number of reoptimized radiation treatment plans that were calculated as described herein. For example, while in some embodiments there may only be one (best) plan generated, in other embodiments there may be multiple plans generated and some may be different than others, but all still meet the prescription. The clinician can then have the option to select from these reoptimized radiation treatment plans. In other embodiments, the best radiation treatment plan can be selected by the system based on an algorithm, for example, considering the prescription and optionally the relative importance of individual criteria in the prescription.

The process may include, at 390, performing an independent dose computation for the selected plan. In some embodiments, radiation planning quality assurance can include utilizing different independent (i.e., using different algorithms and methods) dose calculation software than was used to evaluate validity of creation/selection of the reoptimized radiation treatment. The re-computation of dose with an independent algorithm can be performed to ensure that independent methods agree on the dose values for safety assurance. For example, the independent dose computation can utilize verified software specifically entrusted to accurately compute the dose that will be delivered by the selected reoptimized radiation therapy plan. The independent dose computation can be performed on a different software module of the disclosed system or can be provided to an outside computer that will perform the independent dose computation and return results for storage and display to users of the disclosed system.

As described herein, numerous embodiments include comparisons between prescription doses and the predicted doses for a particular radiation treatment plan. While such comparisons can be completely internal to the disclosed software (i.e., never seen by a user), in some embodiments the system can be configured for computation and displaying of prescription doses and/or criteria to the anatomical structures concurrently with the displaying of the predicted doses. For example, there can be a table having columns representing prescription and predicted doses for radiation treatment plans. The table can have rows that can further break down the displayed doses by anatomical structure for a total dose to a patient. Also, some embodiments can include highlighting or other visual indicia such as color coding to indicate whether a predicted dose is above, below, or within the range or parameter set forth by the prescription.

In certain circumstances, doctors and clinicians may wish to revise aspects of the original treatment plan or one of the reoptimized treatment plans. For example, they may wish to shift the patient couch or revise the contours that have been drawn around the targets or other organs. As described further below, the disclosed software can provide for additional treatment plan reoptimization by enabling clinicians to view aspects of one or more radiation treatment plans and modify them or control the software to perform reoptimization based on updated parameters. This providing for additional treatment plan reoptimization can thus include generation of a new reoptimized radiation treatment plan or modification of one of the automatically generated reoptimized radiation treatment plan(s). The viewing/modifying of reoptimized radiation treatment plans can be facilitated by an interactive graphical user interface provided at control console or any remote computer. Such interfaces can permit changing of radiation treatment plan parameters, anatomical contours, the patient prescription, etc.

Figure 4:
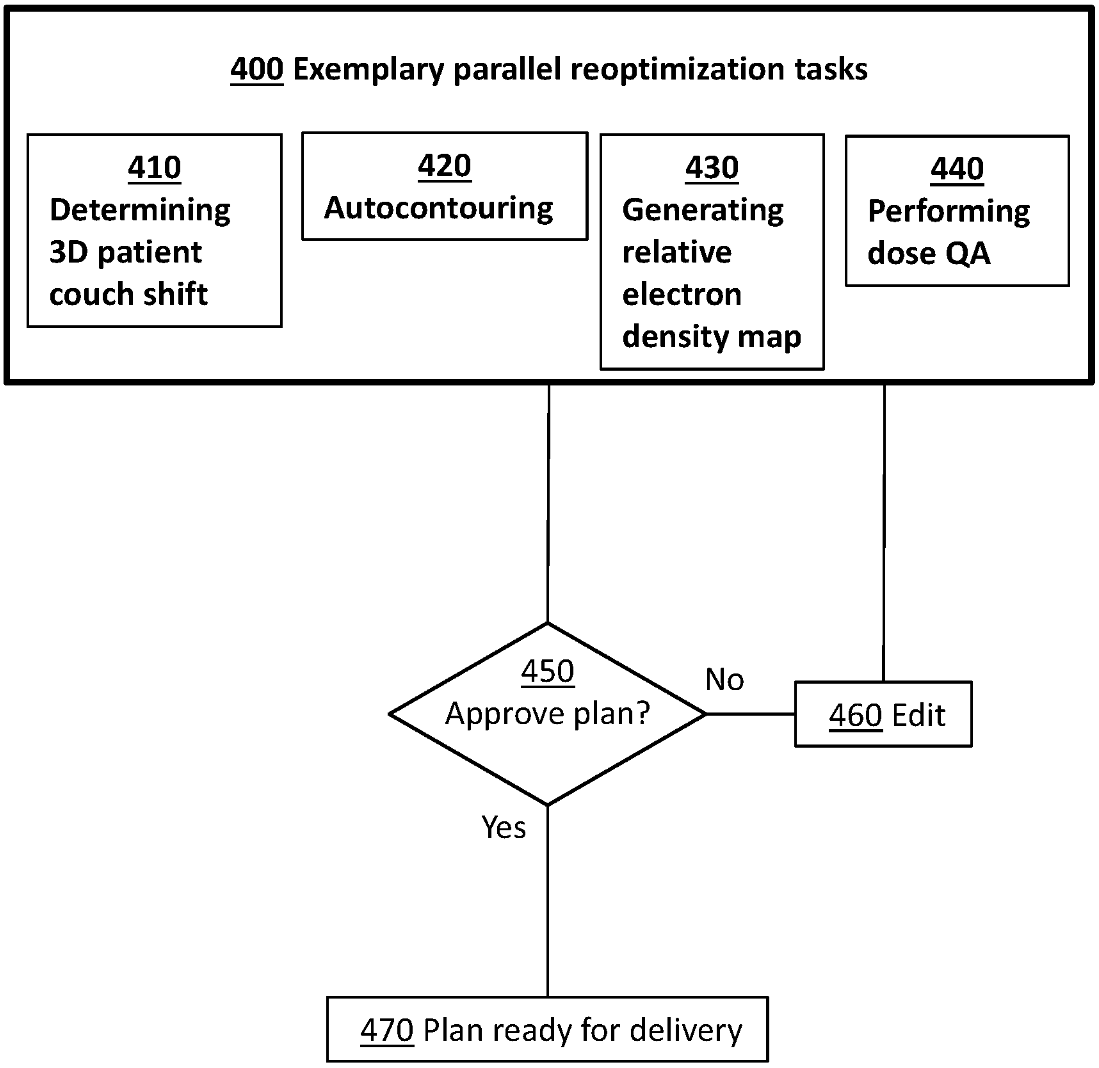
FIG. 4 is a flowchart of exemplary reoptimization tasks that can be performed in parallel by the disclosed software in accordance with certain aspects of the present disclosure.

FIG. 4 depicts examples of reoptimization tasks 400 that can be performed in parallel to speed the creation of a final reoptimized radiation treatment plan. The present disclosure contemplates that the software and system can provide for additional treatment plan reoptimization by enabling clinicians to perform different reoptimization tasks simultaneously. While the particular reoptimization tasks described herein can be part of the parallel operations enabled by the software, the present disclosure also contemplates general systems and software allowing for the parallelization of various tasks related to radiotherapy planning treatment.

Reoptimization processes 400 can include, at 410, software receiving input from a first clinician regarding a 3D patient couch shift. This can include not just modifying the coordinates or orientation of the patient couch but may also include analysis of the effect of potential couch shifts on the quality of image registration (e.g., based on quantitative metrics such as image correlations, predicted dose, etc., to determine the efficacy of the patient couch shift).

At 420, the software can receive input from a second clinician tasked with adjusting contours around patient anatomy. This can include, for example, modifying contouring performed by the software to edit/correct displayed contours to better match the anatomical structures depicted in patient images. Examples of such modifications can include adding/removing portions of an area bounded by a contour. Such editing can be performed in a 2D image or in a number of 2D images that together form part of a 3D patient volume. In some embodiments, the providing for additional treatment plan reoptimization includes enabling multiple clinicians to perform autocontouring simultaneously. For example, there may be 20 anatomical structures that are contoured and they may be divided amongst two (or more) remote computers for clinicians to simultaneously edit their assigned contours. The contours can be stored at the server and may be continuously updated based on changes to individual contours that are made at remote computers are transmitted to the server.

At 430, the software can receive input from a third clinician to generate a relative electron density map. A relative electron density map can be displayed and edited by the third clinician to adjust the values to better represent the particular matter in the image (e.g., adjusting the electron densities to be proper for regions considered to be bone, fat, cancerous tissue, etc.). Adjustments to the relative electron density map can be reflected in predicted dose calculations for the various patient anatomical structures.

At 440, the software can receive input from a fourth clinician tasked with performing radiation dose QA. Based on the radiation treatment plan (e.g., being generated/modified in parallel by the above clinicians) the software can calculate predicted radiation dose to anatomical structures and display them for the evaluating clinician. The clinician can then determine whether the predicted dose is being accurately calculated, for example, by comparing with an independent dose calculation for the radiation treatment plan. The clinician can then electronically advise the other clinicians performing the reoptimization tasks such that the radiation treatment plan passes or fails the required quality assurance checks.

The software provides for additional treatment plan reoptimization by enabling clinicians to attempt different reoptimization strategies simultaneously. For example, IMRT treatment plan objectives can be set or modified with different strategies by different clinicians for both target coverage and sparing of critical organs to meet the prescription. For example, the system can be configured to receive and process inputs from one clinician for exploring higher importance weights for a critical organ while other inputs from another clinician can explore lower importance weights for a target, so both approaches can be efficiently compared. If the prescription is unable to be met, then one strategy may be to change/relax the prescription to allow treatment. Another strategy may be to delay therapy until the patient's organs geometry is adjusted. For example, the patient may move around, such as to settle/adjust fluid or waste distributions and return to the patient couch. Or, the patient may return for treatment on a different day, such as to allow for digestion of food causing organ displacement.

At 450, the software can require approval of certain changes or a final plan approval. Thus, in some embodiments, the software can be configured to receive input from a clinician approving the selected radiation treatment plan. For example, a clinician can be required to approve use of the initial radiation treatment plan, the reoptimized radiation treatment plan that has been selected or, as shown in FIG. 4, approval of a plan that has been reoptimized through the parallel interface described herein. Whether the plan is ready for delivery or requires further editing can be determined based on the approval.

At 460, if approval is not given, or specifically denied, then system can permit further editing of one or more aspects of the available radiation treatment plans (e.g., original or reoptimized) according to any of the embodiments of the present disclosure. For example, any of the above elements of 410-440, or others, can be edited or re-executed based on user input. In some embodiments, the system can display one or more images from the available radiation treatment plans at one or more of the remote computers. The system can receive user input from any of these remote computers approving the images and/or the radiation treatment plan(s). Alternatively, the system can receive user input modifying, or suggesting a modification of, one or more of the reoptimized radiation treatment plan(s). For example, the system can be configured to cause modification of the radiation treatment plan based on user input such as changing contours around anatomical structures, prescription parameters, locations of imaging planes, etc.

For the example of moving an imaging plane, user input can specify that an imaging plane should be moved to a certain location such that a particular anatomical structure (or portion thereof) is (or is not) captured in the images that will be acquired during treatment or used for radiation treatment plan generation. In some embodiments, the system can update the reoptimized radiation treatment plans(s) based on the user input. Because radiation treatment plans are generated based on available imaging (e.g., the targets and other anatomical structures are particular to a given image in a chosen plane) any user input that changes/moves such imaging planes therefore can be the basis of an updated reoptimized radiation treatment plan. For example, suppose a given image plane through the patient shows the target but not a nearby anatomical structure that the prescription wants to avoid delivering radiation to. A reoptimized radiation treatment plan may then determine treatment parameters such as number of beams, their delivery vectors, etc., such that the target receives radiation, but because the structure to be avoided is not in the image, the reoptimized radiation treatment plan may not necessarily account for the nearby anatomical structure. However, upon receiving input moving the imaging plane to another location, it is possible that the anatomical structure is now in the imaging plane. Accordingly, the system can reoptimize the radiation treatment plan and presumably find different solutions for the delivery of radiation to the target—now taking into account the nearby anatomical structure where radiation delivery is to be avoided. Similarly, radiation treatment plans can include gating parameters, and changing the imaging plane for gating can result in an altered treatment plan and delivery.

In other embodiments, imaging parameters can be modified by user input with examples of such imaging parameters including patient orientation, field-of-view, number of imaging planes, what planes to track, plane locations, and imaging resolution. Changing any combination of the imaging planes/parameters can thus similarly serve as the basis for the system modifying a reoptimize radiation treatment plan as explained above.

In other embodiments, the system can be configured to receive user input modifying one or more of tracking parameters, dose parameters, structure shapes, or boundary parameters utilized by the system when controlling the radiation therapy device to deliver the radiation. Examples of tracking parameters can include specifying a degree of how much anatomical structures deform, whether an anatomical structure is stationary or moving, a field of view for the imaging, and imaging parameters (such as described above). Examples of dose parameters can include the prescription whereby the prescription includes limits and ranges of acceptable radiation delivery. Structure shapes can include contours around anatomical structures, for example, contours that specify the gross tumor volume (GTV) or any other contours that have been generated around anatomical structures of interest. Boundary parameters can include specifying regions around anatomical structures that may be used for planning purposes, sometimes referred to as a planning target volume (PTV). For example, a boundary perimeter for a given anatomical structure can be set to include 5% more area or volume resulting in the system generating a slightly expanded perimeter around the identified anatomical structure to allow for a greater permissible region that can receive radiation.

At 470, if approval is given, the system may designate the selected radiation treatment plan as ready for delivery. This can include, for example, automatically delivering the radiation treatment plan as described herein to facilitate the system's ability to deliver radiation treatment in a minimum amount of time.

In the following, further features, characteristics, and exemplary technical solutions of the present disclosure will be described in terms of items that may be optionally claimed in any combination:

Item 1: A non-transitory, machine-readable medium storing instructions which, when executed by at least one programmable processor, cause the at least one programmable processor to perform operations comprising controlling an MRI system to perform treatment-day scans of a patient on a treatment couch prior to treatment; automatically initializing the treatment-day scans; controlling the MRI system to perform the treatment-day scans according to the recalled imaging parameters; automatically generating at least one reoptimized radiation treatment plan; displaying predicted doses to anatomical structures of the patient based on the at least one reoptimized radiation treatment plan; and controlling a radiation therapy device to deliver radiation according to a selected radiation treatment plan.

Item 2: The machine-readable medium of Item 1, wherein the automatic initializing of the treatment-day scans is based on a sensor indicating a door to a treatment room is closed.

Item 3: The machine-readable medium of any one of the preceding Items, the operations further comprising: sensing that the patient is positioned at isocenter; wherein the automatic initializing of the treatment-day scans is based on the sensing of the patient at isocenter.

Item 4: The machine-readable medium of any one of the preceding Items, wherein the imaging parameters specify imaging types comprising one or more of volumetric, 4D volumetric, and real-time 4D volumetric.

Item 5: The machine-readable medium of any one of the preceding Items, wherein the imaging parameters specify one or more of contrast, dimensionality, frame rate, resolution, field of view, order of scanning.

Item 6: The machine-readable medium of any one of the preceding Items, the automatically generating of the at least one reoptimized radiation treatment plan further comprising: performing autocontouring of the anatomical structures of the patient; computing a relative electron density map; computing a 3D patient table shift; and calculating the predicted doses to the anatomical structures.

Item 7: The machine-readable medium of any one of the preceding Items, the automatically generating of the at least one reoptimized radiation treatment plan further comprising: generating reoptimized radiation treatment plans based on modifying treatment plan generation parameters, the generating stopping when one of the reoptimized treatment plans meets a treatment prescription or when a predetermined number of reoptimized radiation treatment plans are generated.

Item 8: The machine-readable medium of any one of the preceding Items, the operations further comprising: receiving input changing one or more features of the at least one reoptimized radiation treatment plan; and automatically recalculating the at least one reoptimized radiation treatment plan based on the changed features.

Item 9: The machine-readable medium of any one of the preceding Items, the operations further comprising: displaying prescription doses to the anatomical structures concurrently with the displaying of the predicted doses.

Item 10: The machine-readable medium of any one of the preceding Items, the operations further comprising: imaging during treatment by the MRI system performing one or more of 2D imaging, multiplanar 2D imaging, 3D imaging, 4D imaging, and real-time 4D volumetric imaging; wherein the controlling of the radiation therapy device is further based on the imaging.

Item 11: The machine-readable medium of any one of the preceding Items, the operations further comprising: automatically calculating and displaying information for controlling the radiation therapy device based on the imaging.

Item 12: The machine-readable medium of any one of the preceding Items, wherein the information comprises one or more of: imaging dimensionality, imaging parameters, tissue-tracking boundaries type and generation parameters, and tissue-tracking algorithm parameters.

Item 13: The machine-readable medium of any one of the preceding Items, the operations further comprising providing for additional treatment plan reoptimization.

Item 14: The machine-readable medium of any one of the preceding Items, wherein providing for additional treatment plan reoptimization includes generation of a new reoptimized radiation treatment plan, or modification of one of the automatically generated reoptimized radiation treatment plan(s).

Item 15: The machine-readable medium of any one of the preceding Items, wherein providing for additional treatment plan reoptimization includes enabling clinicians to perform different reoptimization tasks simultaneously.

Item 16: The machine-readable medium of any one of the preceding Items, wherein providing for additional treatment plan reoptimization includes enabling multiple clinicians to perform autocontouring simultaneously.

Item 17: The machine-readable medium of any one of the preceding Items, wherein providing for additional treatment plan reoptimization includes enabling clinicians to attempt different reoptimization strategies simultaneously.

Item 18: The machine-readable medium of any one of the preceding Items, wherein providing for additional treatment plan reoptimization includes the system receiving user input modifying one or more of the reoptimized radiation treatment plan(s).

Item 19: The machine-readable medium of any one of the preceding Items, the operations further comprising: moving an imaging plane included in the one or more of the reoptimized radiation treatment plan(s) based on the user input; and updating the one or more of the reoptimized radiation treatment plan(s) based on a new location of the imaging plane.

Item 20: The machine-readable medium of any one of the preceding Items, further comprising: receiving user input modifying one or more of tracking parameters, dose parameters, structure shapes, or boundary parameters utilized by the system when controlling the radiation therapy device to deliver the radiation.

Item 21: The machine-readable medium of any one of the preceding Items, the operations further comprising receiving input from a clinician approving the selected radiation treatment plan.

Item 22: A method comprising the operations of any of any one of the preceding Items.

Item 23: A system comprising: at least one programmable processor; and a non-transitory, machine-readable medium storing instructions which, when executed by at least one programmable processor, cause the at least one programmable processor to perform operations comprising those of any one of Items 1-21.

Although a few embodiments have been described in detail above, other modifications are possible. For example, the elements depicted in FIGS. 2-4 and described herein do not require the particular order shown, or sequential order, to achieve desirable results.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention (s), and their equivalents, that are protected thereby.

What is claimed is:

1. A non-transitory, machine-readable medium storing instructions which, when executed by at least one programmable processor, cause the at least one programmable processor to perform operations comprising:

automatically recalling imaging parameters from computer memory for controlling an MRI system to perform treatment-day scans of a patient on a treatment couch prior to treatment;

automatically initializing the treatment-day scans for execution according to the recalled imaging parameters, wherein the automatically initializing occurs without user input and is performed when sensing a treatment-day scanning trigger;

automatically controlling the MRI system to perform the treatment-day scans according to the recalled imaging parameters;

automatically generating at least one reoptimized radiation treatment plan;

displaying predicted doses to anatomical structures of the patient based on the at least one reoptimized radiation treatment plan; and controlling a radiation therapy device to deliver radiation according to a selected radiation treatment plan.

2. The machine-readable medium of claim 1, wherein the automatic initializing of the treatment-day scans is based on a sensor indicating a door to a treatment room is closed.

3. The machine-readable medium of claim 1, the operations further comprising: sensing that the patient is positioned at isocenter;

wherein the automatic initializing of the treatment-day scans is based on the sensing of the patient at isocenter.

4. The machine-readable medium of claim 1, wherein the imaging parameters specify imaging types comprising one or more of volumetric, 4D volumetric, and real-time 4D volumetric.

5. The machine-readable medium of claim 1, wherein the imaging parameters specify one or more of contrast, dimensionality, frame rate, resolution, field of view, order of scanning.

6. The machine-readable medium of claim 1, the automatically generating of the at least one reoptimized radiation treatment plan further comprising:

performing autocontouring of the anatomical structures of the patient;

computing a relative electron density map;

computing a 3D patient table shift; and calculating the predicted doses to the anatomical structures.

7. The machine-readable medium of claim 1, the automatically generating of the at least one reoptimized radiation treatment plan further comprising:

generating reoptimized radiation treatment plans based on modifying treatment plan generation parameters, the generating stopping when one of the reoptimized treatment plans meets a treatment prescription or when a predetermined number of reoptimized radiation treatment plans are generated.

8. The machine-readable medium of claim 1, the operations further comprising: receiving input changing one or more features of the at least one reoptimized radiation treatment plan; and automatically recalculating the at least one reoptimized radiation treatment plan based on the changed features.

9. The machine-readable medium of claim 1, the operations further comprising: displaying prescription doses to the anatomical structures concurrently with the displaying of the predicted doses.

10. The machine-readable medium of claim 1, the operations further comprising: imaging during treatment by the MRI system performing one or more of 2D imaging, multiplanar 2D imaging, 3D imaging, 4D imaging, and real-time 4D volumetric imaging;

wherein the controlling of the radiation therapy device is further based on the imaging.

11. The machine-readable medium of claim 1, the operations further comprising: automatically calculating and displaying information for controlling the radiation therapy device based on the imaging.

12. The machine-readable medium of claim 11, wherein the information comprises one or more of: imaging dimensionality, imaging parameters, tissue-tracking boundaries type and generation parameters, and tissue-tracking algorithm parameters.

13. The machine-readable medium of claim 1, the operations further comprising providing for additional treatment plan reoptimization.

14. The machine-readable medium of claim 13, wherein providing for additional treatment plan reoptimization includes generation of a new reoptimized radiation treatment plan, or modification of one of the automatically generated reoptimized radiation treatment plan(s).

15. The machine-readable medium of claim 13, wherein providing for additional treatment plan reoptimization includes enabling clinicians to perform different reoptimization tasks simultaneously.

16. The machine-readable medium of claim 13, wherein providing for additional treatment plan reoptimization includes enabling multiple clinicians to perform autocontouring simultaneously.

17. The machine-readable medium of claim 13, wherein providing for additional treatment plan reoptimization includes enabling clinicians to attempt different reoptimization strategies simultaneously.

18. The machine-readable medium of claim 13, wherein providing for additional treatment plan reoptimization includes the system receiving user input modifying one or more of the reoptimized radiation treatment plan(s).

19. The machine-readable medium of claim 18, the operations further comprising: moving an imaging plane included in the one or more of the reoptimized radiation treatment plan(s) based on the user input; and updating the one or more of the reoptimized radiation treatment plan(s) based on a new location of the imaging plane.

20. The machine-readable medium of claim 1, further comprising:

receiving user input modifying one or more of tracking parameters, dose parameters, structure shapes, or boundary parameters utilized by the system when controlling the radiation therapy device to deliver the radiation.

21. The machine-readable medium of claim 1, the operations further comprising receiving input from a clinician approving the selected radiation treatment plan.

22. The machine-readable medium of claim 1, the operations further comprising automatically determining acceptability of the reoptimized radiation treatment plan.

* * * * *